United States Patent [19]

Baldwin

[11] Patent Number: 5,664,559
[45] Date of Patent: Sep. 9, 1997

[54] DOUBLE SHIELD MOUTH-TO-MOUTH RESUSCITATOR MASK WITH BARRIER FOR CONTAMINATED FINGERS

[76] Inventor: Gene R. Baldwin, 324 N. Gardiner Ave., Rockford, Ill. 61107

[21] Appl. No.: 331,693

[22] Filed: Oct. 31, 1994

Related U.S. Application Data

[63] Continuation-in-part of Ser. No. 181,837, Jan. 18, 1994, abandoned.

[51] Int. Cl.$^6$ ............................. A61M 16/00; A62B 7/00
[52] U.S. Cl. ............................. 128/203.11; 128/202.28
[58] Field of Search ............ 128/202.28–203.11, 128/200.24, 204.18, 205.11, 857, 863

[56] References Cited

U.S. PATENT DOCUMENTS

| | | | |
|---|---|---|---|
| 3,021,836 | 2/1962 | Marsden | 128/202.28 |
| 3,356,100 | 12/1967 | Seeler | 128/203.11 |
| 3,626,936 | 12/1971 | Barker | 128/203.11 |
| 4,579,114 | 4/1986 | Gray et al. | 128/203.11 |
| 4,819,627 | 4/1989 | Connors | 128/202.29 |
| 4,819,628 | 4/1989 | Eisenberg et al. | 128/203.11 |
| 4,909,245 | 3/1990 | Wollenhaupt | 128/202.29 |
| 5,005,568 | 4/1991 | Loescher et al. | 128/203.11 |
| 5,088,485 | 2/1992 | Schock | 128/202.28 |
| 5,119,809 | 6/1992 | Gerson | 128/202.28 |
| 5,152,283 | 10/1992 | Yamasaki | 128/202.28 |
| 5,355,877 | 10/1994 | Cheng | 128/203.11 |
| 5,511,543 | 4/1996 | Shirley | 128/202.28 |

FOREIGN PATENT DOCUMENTS

| | | | |
|---|---|---|---|
| 2198957 | 6/1986 | United Kingdom | 128/202.28 |
| 2204498 | 11/1988 | United Kingdom | 128/203.11 |

*Primary Examiner*—Kimberly L. Asher
*Attorney, Agent, or Firm*—Harold A. Williamson

[57] ABSTRACT

The invention is directed to a mouth-to-mouth manually manipulated resuscitation mask of the type having a one-way valve through which air is delivered from an operator's mouth to a victim's mouth and lungs through the valve. The resuscitation mask includes a first flexible barrier. The flexible material is capable of providing a sealing contact with a victim's face in a region adjacent the victims mouth. The flexible material has an opening for a one-way valve. A second flexible barrier in the form of a thin sheet of flexible material has an opening the periphery of which is secured to the first flexible barrier and the valve to thereby provide a spatially separated region between the first and second barriers to thereby isolate the mouth and face of the operator from the area where the operator's fingers/hands make contact on the first flexible barrier. An additional feature of the invention is the provision of a region in the first flexible barrier means having a pre-established elastic memory such that upon release of the manually applied pressure to the first flexible barrier the regions having the pre-established elastic memory initially flexed by the manually applied pressure return to an original unflexed position thereby lifting and unsealing the first flexible barrier from the victim's mouth/face allowing passage of air from the victim's nose and mouth.

4 Claims, 4 Drawing Sheets

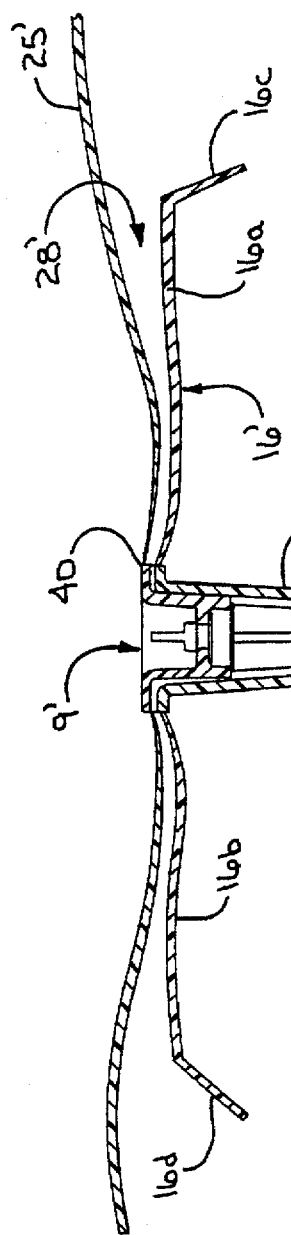
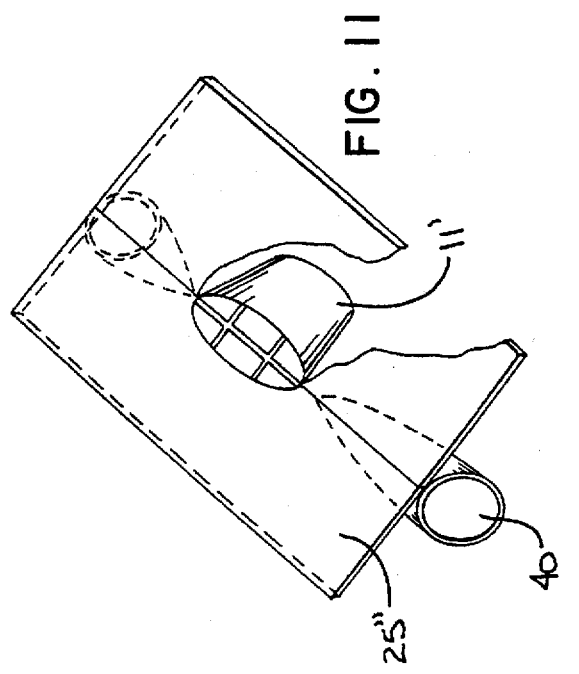
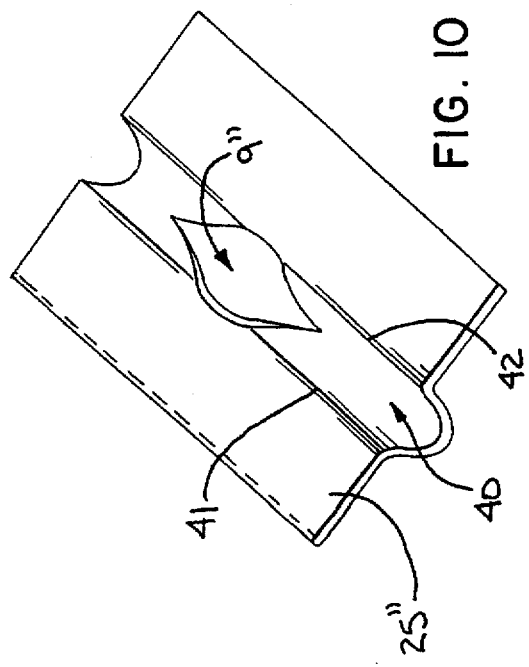

DOUBLE SHIELD MOUTH-TO-MOUTH RESUSCITATOR MASK WITH BARRIER FOR CONTAMINATED FINGERS

This application is a continuation-in-part of U.S. patent application Ser. No. 08/181,837, filed Jan. 18, 1994, now abandoned.

FIELD OF THE INVENTION

Mouth-to-mouth manually manipulated resuscitation devices of the type having a one-way valve through which air is delivered from an operator's mouth to a victim's mouth and lungs through the valve.

BACKGROUND OF THE INVENTION

Many varieties of products have been developed to help prevent or reduce the risk of cross contamination from a victim in need of mouth-to-mouth resuscitation to the person doing the resuscitation. The person doing the resuscitation will be referred to hereinafter as the operator.

A group of these devices are called shields or masks. They generally consist of plastic or other flexible material that is formed or can be formed to take on a mating configuration of the victim's mouth area to provide an air tight seal. These shield or masks may include a one-way valve or filter through which air from the operator passes on the way to a victim's mouth and lungs.

The operator's hands or fingers are initially employed to engage a portion of the device in a region of a victim's mouth to position a flexible portion of the device against the victim's mouth area which provides an air tight seal.

The operator places the lips of their mouth in a sealing relationship with a surface of the device in a region surrounding the valve or filter. The valve or filter is positioned over the opened mouth of the victim. The operator blows through the valve or filter and his breath passes into the victim's mouth and hence into the victim's lungs. This is followed by the operator releasing his mouth from the surface of the device thereby releasing the air tight seal formed by the device. This release of pressure allows the victim's breath to exit the victim's mouth whereupon the cycle is repeated until the victim regains consciousness.

It should be noted that in today's world there is a mortal fear that any close or intimate contact with body fluids of an individual stricken with the acquired immune deficiency syndrome (AIDS) or tuberculosis could result in the transmission and infection to a rescuer of these deadly maladies.

Various devices have been devised to shield the rescuer when applying mouth-to-mouth resuscitation.

For example the Sherman U.S. Pat. No. 3,802,428 ('428) issued Apr. 9, 1974 discloses a mouth-to-mouth resuscitator comprised of a flexible face mask having a central opening formed therein which extends over the mouth area of the person administering artificial respiration. A flexible tubular member is attached to the periphery of the central opening and depends therefrom for placement in the mouth of the victim. The tubular member acts as a one-way valve and inflates when delivering air and collapses for preventing any air or fluid flow in the reverse direction.

A disadvantage of this design is that the operator's fingers may become contaminated during resuscitation. Because the operator's fingers are needed to hold or position the flexible face mask in place, contamination is likely to be transferred from the operator's fingers to the top surface of the mask where the operator places his mouth.

It is very common during a resuscitation procedure to remove and reposition the mask should the victim vomit. This makes it nearly impossible to prevent contamination from being transferred to the operator's mouth side of the mask during this type of mask handling.

The Eisenberg et al U.S. Pat. No. 4,819,628 ('628) issued Apr. 11, 1989 shows and defines another typical prior art device, which is described as an improvement over the Sherman patent referred to next above. The Eisenberg et al device includes a flexible sheet having an opening centrally formed therein and a rigid tube secured to the sheet around the periphery of the opening for insertion into a mouth of a victim. A self closing one-way valve is contained in the tube and extends downward from the sheet opening. The operator exhales a deep breath into an input of the one-way valve thereby forcing the operator's exhaled air into the mouth of the victim. The one-way valve prevents any back flow of air, mist or liquid from the victim to the operator. Grooves are formed in the victim's side of the sheet to provide air pathways to the outside for air exhaled by the victim. A patch of an irregular non-smooth surface is also formed on the victim's side of the sheet to prevent the sheet from clinging to the nose of the victim and restricting air flow from the nose.

The subject invention distinguishes over the '428 and '628 patent in that these patents fail to entertain the fact that victims frequently have regurgitated fluids which must be cleared from the victim's mouth region with fingers or the hands of the operator prior to inserting the device's rigid one-way valve into the victim's mouth. Clearing away regurgitated matter and mucous from the mouth area of the victim frequently causes the operator's hands to be covered with regurgitated matter and mucous which may be transferred to the face and mouth area of the operator.

The instant invention includes a secondary flexible barrier interposed between the operator's fingers and hands to shield the mouth and face of the operator from the victim's regurgitated matter and mucous. No suggestion of this inventive feature is found in either the '428 or '628 patents.

The subject invention also takes cognizance of the fact that when the mouth and face of the victim are covered with regurgitated matter and mucous the air pathways and non smooth surface provided in the '628 fail to provide a quick release of the flexible sheet from the victim's face. This failure to provide a quick release restricts the passage of exhaled air from the victim's mouth and nose. As a consequence of this type of air flow restriction the tempo i.e. the rhythm of operator's respiration efforts are hampered and the victim's chances of being successfully resuscitated are diminished.

SUMMARY OF THE INVENTION

The invention is directed to a mouth-to-mouth manually manipulated resuscitation mask of the type having a one-way valve through which air is delivered from an operator's mouth to a victim's mouth and lungs through the valve. The resuscitation mask includes a first flexible barrier. The flexible material is capable of providing a sealing contact with a victim's face in a region adjacent the victims's mouth. The flexible material has an opening for a one-way valve.

In a preferred embodiment of the invention, a second flexible barrier in the form of a thin sheet of flexible material has an opening the periphery of which is secured to the first flexible barrier and the valve to thereby provide a spatially separate region between the first and second barriers to thereby isolate the mouth and face of the operator from the area where the operator's fingers/hands make contact on the first flexible barrier.

An additional feature of the invention is the provision of a region in the first flexible barrier means having a pre-established elastic memory such that upon release of the manually applied pressure to the first flexible barrier the regions having the pre-established elastic memory initially flexed by the manually applied pressure return to an original unflexed position thereby lifting and unsealing the first flexible barrier from the victim's mouth/face allowing passage of air from the victim's nose and mouth.

It is therefore a primary object of this invention to provide a resuscitation mask that greatly reduces the risk of contamination from a victim's mouth from being transferred by the hand(s) of the operator to the operator's mouth while performing the resuscitation.

It is therefore another object of the invention to provide a mouth-to-mouth manually manipulated resuscitation mask that allows an operator's fingers and hands that holds the mask to remove and reposition the mask under a protective shield or barrier without the need to touch or position the operator's fingers on the side where the operator's mouth is placed.

Yet another object of the invention is the provision of a mouth-to-mouth resuscitation mask that includes a region having a pre-established elastic memory that when flexed allows for an air tight seal to be formed with a victim's face. The region having the pre-established elastic memory when unflexed interrupts the mask to face seal allowing the ready passage of air from the victim's mouth and nose to a point outside the mask.

A further object of the invention is the provision of a mouth-to-mouth resuscitation mask that includes a flexible member capable of providing contact with a face of a victim. The flexible barrier is also provided which has an opening a periphery of which is secured to the one-way valve to thereby provide a spatially separated region between the flexible member and the flexible barrier to thereby isolate the mouth and face of the operator from the hand(s) of the operator that manually apply pressure on the flexible member to position the flexible member and said one-way valve.

BRIEF DESCRIPTION OF THE DRAWINGS

The description set forth above, as well as other objects, features and advantages of the present invention, will be more fully appreciated by referring to the detailed description and the drawings that follow. The description is of the presently preferred but, nonetheless, illustrative embodiment in accordance with the present invention, when taken in conjunction with the accompanying drawing wherein:

FIG. 9 is a three dimensional view of the embodiment of the invention depicted in FIG. 9. The three dimensional showing illustrates the mask inverted with respect to FIG. 8, and FIG. 10 and FIG. 11 depict yet another embodiment of the invention.

DETAILED DESCRIPTION OF THE PREFERRED EMBODIMENT

Figure 1:
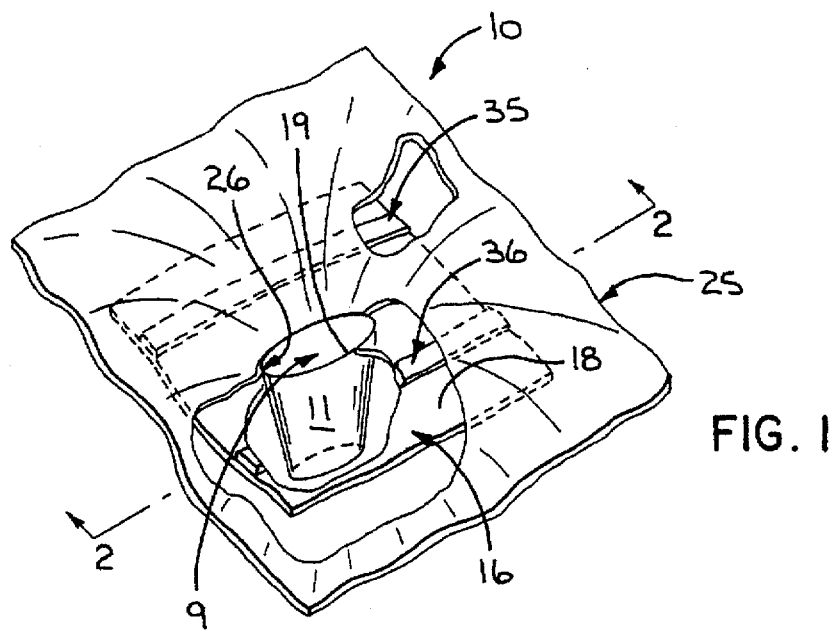
FIG. 1 is a three dimensional illustration of a mask embodying the invention with portions thereof shown broken away.

Reference is now made to FIG. 1 which depicts in a three-dimensional manner all features of the subject invention in a preferred embodiment.

The basic component parts of the mask 10 include as shown centrally disposed in FIG. 1 a one-way valve 11 having the generalized configuration as shown. Details of the one-way valve are not shown. A one-way valve suitable for use in the resuscitator mask 10 embodying the instant invention may be found as shown and described in the M. J. Sherman U.S. Pat. No. 3,802,428 issued Apr. 9, 1974 and the Eisenberg et al U.S. Pat. No. 4,819,628. The details of the one-way valve do not form a part of the instant invention. Accordingly any of a variety of one-way valves may be employed. The one-way valve 11 is inserted into the mouth 12 of a victim 13 as illustrated in FIG. 4.

Figure 4:
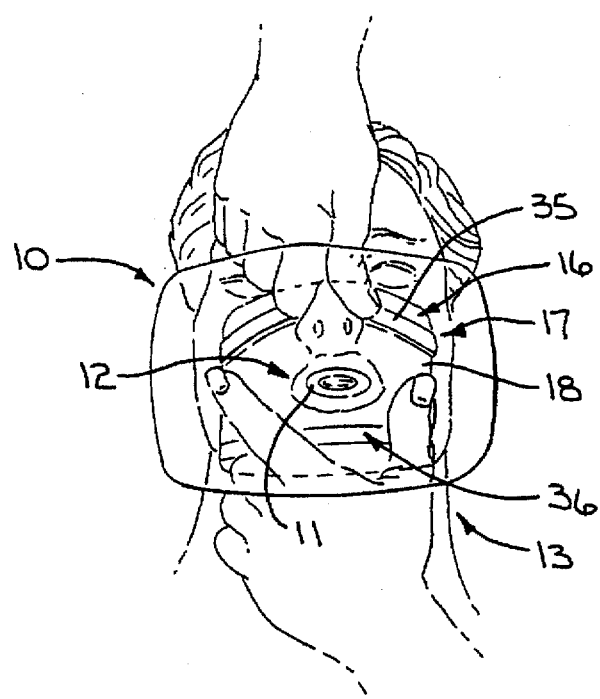
FIG. 4 is an illustration of the subject invention in an operative position on the face of a victim to be resuscitated.

The resuscitator mask 10 further includes a first flexible barrier 16 which is capable of providing a sealing contact with a victim's face 17 (FIG. 4). The flexible barrier 16 is formed from a thin sheet of flexible material which may be transparent and is impermeable by body fluids. An important characteristic of the flexible barrier material is its ability when pressure is applied to an upper surface 18 (see FIGS. 2 and 4) that it conform to the contour of the victims face 17 in the region where the pressure is applied. Preferably, the flexible barrier 16 is made of a flexible plastic material such as a polyvinyl chloride (PVC) or similar material such as film forming thermoplastics including nylon, polyethylene, polypropylene, polyvinyl acetate; soft cellulose acetate, etc.

Figure 2:
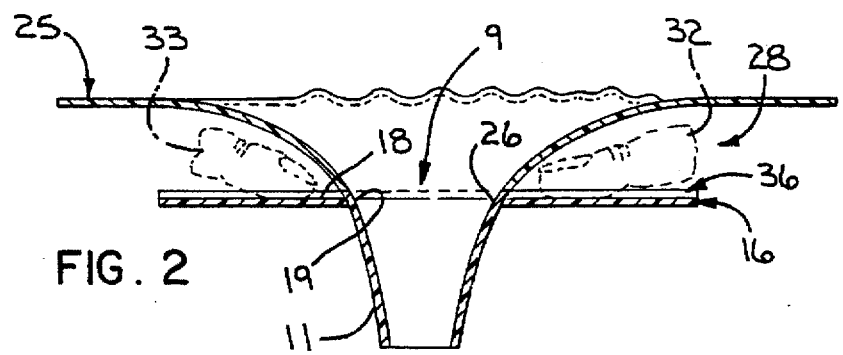
FIG. 2 is a view taken along line 2—2 in FIG. 1.
Figure 3:
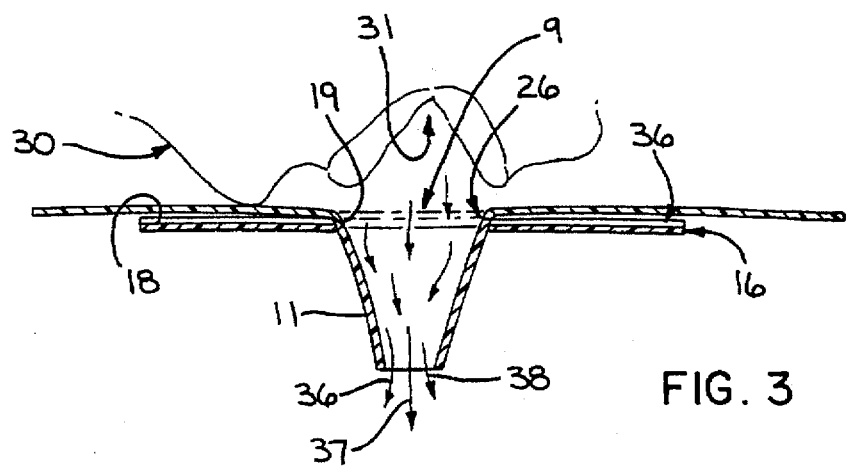
FIG. 3 is a cross-section of a mask embodying the invention prior to use on a victim.

A preferred embodiment of the invention the flexible barrier 16 has an opening 9 and is integrally coupled to a perimeter 19 of one-way valve 11 as best seen in FIGS. 1, 2 and 3. In the event that one-way valve 11 is a thermoplastic the integral coupling may be attained by the application of heat and pressure to the first flexible barrier 16 where the barrier 16 contacts the perimeter 19 of the one-way valve 11. Suitable adhesives may also be employed to form the integral coupling.

A second flexible barrier 25 is also provided with a central opening (not referenced) which is coincident with and integrally secured as indicated by arrow and associated reference numeral 26 to the first flexible barrier 16 and the perimeter 19 of the one-way valve 11. The second flexible barrier 25 may be integrally coupled to the one-way valve 11 and the first flexible barrier 16 at the one-way valve perimeter 19 in a manner similar to that described next above in respect of barrier 16 and one-way valve 11.

This just described arrangement of the first flexible barrier 16, one-way valve 11 and second flexible barrier 25 cooperate to create a means that provides a spatially separated place, space or region 28 best seen in FIG. 2. This space/place/region providing means is adapted to engage an operators fingers 32, 33 FIG. 2 from the operator's mouth 31, FIG. 3. The invention is also embodied in other arrangements where a first and second flexible barrier are arranged to provide a similar protective region as will be described with respect to FIGS. 5, 6 and 7.

Attention is now directed to FIG. 2 and 3 which show in a line drawing (FIG. 3) the profile 30 of an operator. The mouth 31 of the operator is positioned above the second flexible barrier 25 to thereby isolate the mouth 31 of the operator from the operator's hands, here shown in FIG. 2 in broken line only as fingers 32, 33. The fingers 32, 33, FIG. 2, manually apply pressure on the first flexible barrier 16 to position it on the victim's face 17 (see FIG. 4). In FIG. 3 the mouth 31 of the operator is shown delivering air (see air flow arrows 36, 37, 38) through the one-way valve 11. The pressure of the operator's mouth against the mask as the mouth 31 in FIG. 3 is about to provide, creates a sealing force to hold the mask against the victim's face 17 (see FIG. 4).

Attention is again directed to FIG. 1 specifically and FIGS. 2, 3 and 4 generally. The first flexible barrier 16 has shown transversely positioned a pair of regions 35, 36 that have a pre-established elastic memory such that upon release of the manually applied pressure the first flexible barrier 16, the regions 35, 36 cause the lifting and unsealing of the first flexible barrier 16 from the victim's face 17 (FIG. 4) allowing passage of air from the victim's mouth 12. The regions 35, 36 may be formed of plastic strips bonded to the flexible barrier 16 by any suitable means.

Figure 5:
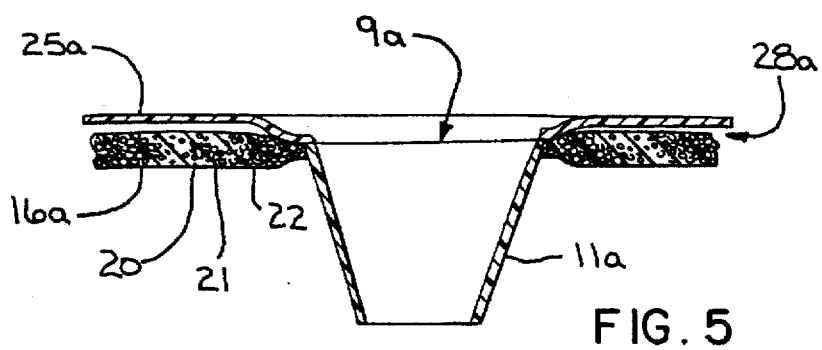
FIG. 5 depicts in a partial cross-section an embodiment of the invention which include a resilient air pillow flexible barrier having an inherent elastic memory.
Figure 6:
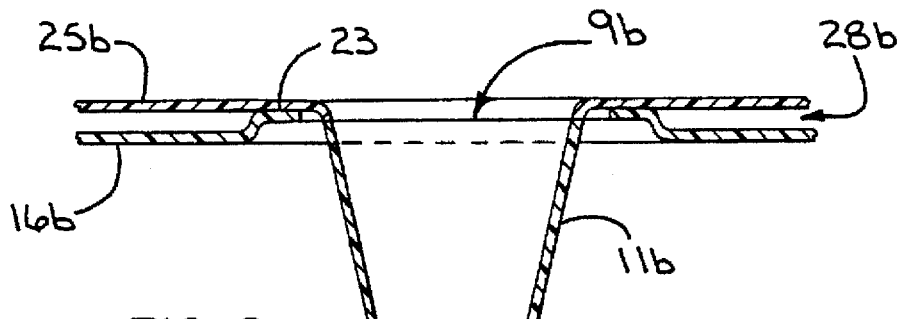
FIG. 6 and 7 show a variety of integral connections between flexible barriers and a one-way valve which embody the invention.
Figure 7:
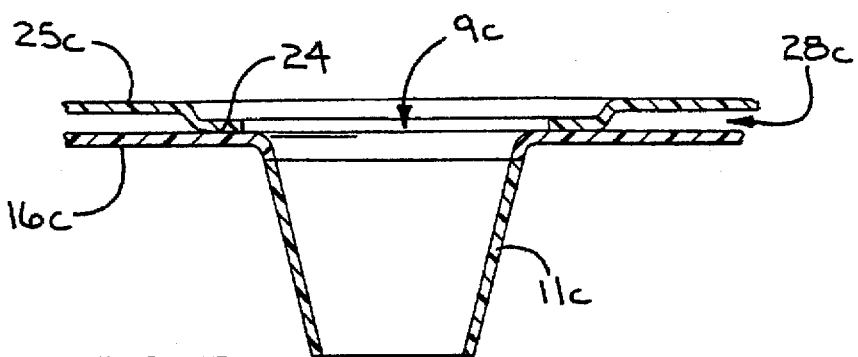

In FIG. 5 as well as FIGS. 6, 7, 8, 9, 10 and 11 identical reference numerals are employed as in the earlier figures to designate similar items. In FIGS. 5, 6 and 7 reference numerals will have added to them letter characters a, b and c to distinguish respectively between FIGS. 5, 6 and 7.

Figure 5A:
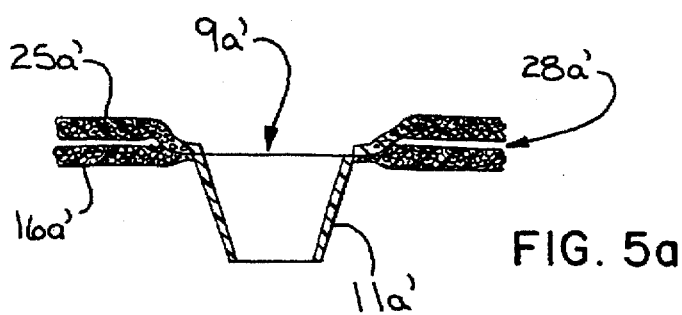
FIG. 5a illustrates in a partial cross-section an embodiment of the invention which includes a pair of flexible barriers each having an inherent elastic memory.

Reference is now made to FIG. 5 which illustrates a cross-section of a portion of another embodiment of the invention. This embodiment of the invention includes a first flexible barrier 16a and a second flexible barrier 25a each integrally coupled to one-way valve 11a in a manner similar to that described in FIGS. 1–3. The point of novelty present in this embodiment of the invention resides in the nature of the construction of first flexible barrier 16a such that the entire flexible barrier 16a is provided with a pre-established elastic memory created by encapsulating air in the flexible barrier. Entrapped gas or air is indicated by reference numerals 20, 21, 22, in the thermoplastic material of which the flexible barrier 16a is composed. The presence of the air in the plastic cause the overall first flexible layer to yieldingly resist flexing when the barrier 16a is pressed against the face of the victim when the operator's mouth is applied to the second flexible barrier 25a. After the operator has exhaled into the victim's mouth via the one-way valve 11a and then released downward pressure of his lips from the second flexible barrier 25a, the first flexible barrier 16a returns to its initial unflexed condition thereby allowing exhaled air from a victim's mouth to easily escape to a region outside the mask. FIG. 5a is similar to FIG. 5 in that the invention contemplates as being within the spirit of the invention a second flexible barrier 25a' constructed to include a pre-set elastic memory.

FIGS. 6 and 7 are partial cross-sections respectively of first flexible barriers 16b, 16c; second flexible barrier 25b, 25c and one-way valve 11b, 11c. In FIG. 6 it will be observed that the spatially separated region 28b is created by securing the first flexible barrier 16b to the second flexible barrier 25b at a point 23 on an under surface of the second flexible barrier 25b, whereas in FIG. 7 the second flexible barrier 25c is secured to the first flexible barrier at a point 24 on an upper surface of the first flexible barrier 16c.

Figure 8:
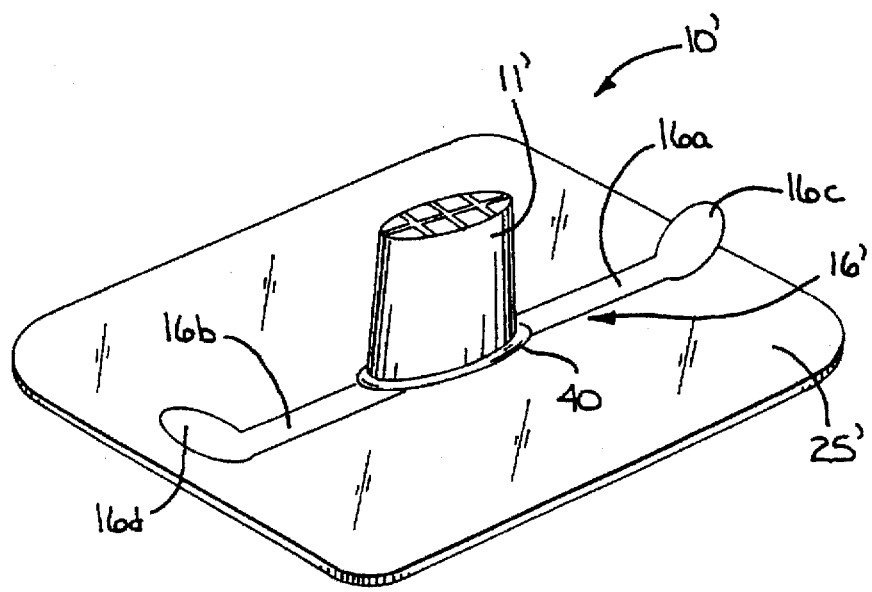
FIG. 8 is crossectional illustration of another embodiment of the invention.

Reference is now made to FIGS. 8 and 9 which when taken together illustrate another embodiment of the invention. An overall feeling of the nature of this embodiment of the invention will be readily apparent if attention is first directed to FIG. 9 which shows a resuscitation mask 10' inverted so as to show a one-way valve 11' pointing upward as shown in this figure. Two other basic components of the mask, namely, a flexible elongated member 16' and a flexible barrier sheet 25' are also shown.

The flexible elongated member 16', as shown in both FIGS. 8 and 9, extends on either side of the one-way valve 11' and is secured to the one-way valve 11'. The nature of the joining of the flexible elongated member 16' to the one-way valve 11' and/or the flexible barrier 25' does not form a part of the invention. Accordingly any suitable bonding technique may be employed.

The flexible, elongated member 16' is comprised of a pair of straps 16a', 16b'. Each strap terminates as shown with tabs 16c' and 16d' respectively. In other words in this embodiment of the invention the flexible elongated member 16' replaces the first flexible barrier 16 in the earlier described embodiments.

The flexible member allows contact with a face of a victim in a region adjacent the victim's nose/mouth (not shown).

The flexible barrier 25' has an opening, a periphery 40 of which is secured to the one-way valve 11'. This just described arrangement provides a spatially separated place or region 28' between the flexible member 16' and the flexible barrier 25 to thereby isolate the mouth and face of an operator from the hand(s)/finger(s) of the operator that mutually apply pressure on the flexible member 16' to position the flexible member 16' and the one-way valve in the mouth/nose region of the victim.

Stated another way, the elongated member 16' and the flexible barrier sheet 25' cooperate to jointly create a means for providing a space/place between the elongated member 16' and the flexible sheet 25' which space/place providing means is adapted to engage an operators fingers and separate an operator's fingers from the operator's mouth. The flexible barrier sheet 25' having portions thereof being capable of being longitudinally distanced from the elongated member 16'.

The flexible member 16' may be fashioned of a material that has a preset elastic memory.

Attention is now directed to FIGS. 10 and 11 where yet another embodiment of the invention is illustrated. In this embodiment a flexible barrier sheet 25" as shown in FIG. 10 is folded so as to provide loop portion 40. Fold lines 41, 42 of the flexible barrier sheet 25 are brought together as shown in FIG. 10 and bonded to create the loop portion 40. This loop portion 40 provides a place that may be engaged by the finger(s)/hand(s) of the operator.

The spirit of the invention also includes the idea of taking a loop of material just described and bonding the inner surface of the loop together to form a protuberance that is downwardly projecting. This would provide a place where the operator's finger(s)/hand(s) would then be able to grasp the protuberance and provide a means adapted to engage an operators fingers and keep separated an operator's fingers from the operator's mouth.

The one-way valve 11 is shown in place in FIG. 10.

From the foregoing detailed description of the invention it should be abundantly clear that the resuscitation mask embodying the invention greatly reduces the risk of contamination from a victim's mouth being spread from the operator's hands while handling the mask to the operator's mouth or mouth area of the device during resuscitation while simultaneously assuring a quick unsealing of the mask from a victim's face to allow passage of the victim's exhaled breath.

Though the invention has been described with respect to a specific preferred embodiment thereof, many variations and modifications will immediately become apparent to those skilled in the art. It is therefore the intention that the appended claims be interpreted as broadly as possible in view of the prior art to include all such variations and modifications.

What I claim is new:

1. A mouth-to-mouth manually manipulated resuscitation mask to reduce risk of contamination being transmitted via fluids from a victim's mouth to a rescuer's mouth during rescue breathing, said resuscitation mask including in combination;

(a) a barrier means for providing a sealing contact with a face of a victim in a region adjacent a victim's mouth, said barrier means is comprised of a sheet of flexible material, said sheet of flexible material having an opening therethrough;

(b) a one-way valve disposed in said opening and sealingly coupled to said sheet of flexible material, and (c) means for a rescuer's fingers to manually hold said sheet of flexible material during repetitive steps of positioning and removing said one-way valve into and out of the mouth of the victim during rescue breathing, said means for manually holding said sheet of flexible material being positioned between said sheet of flexible material and said victim's face thereby allowing said rescuer's fingers, which are contaminated by said fluids from said victim's mouth, to remain beneath said sheet of flexible material during handling of said mask thereby reducing the risk of said contamination coming into contact with said rescuer's mouth.

2. The resuscitation mask of claim 1 wherein said means for a rescuer's fingers to manually hold said sheet of flexible material are elongated strips of flexible material that are physically coupled to said sheet of flexible material and to said one-way valve and extend laterally away from opposing sides of said one-way valve.

3. The resuscitation mask of claim 1 wherein said means for a rescuer's fingers to manually hold said sheet of flexible material is another sheet of flexible material physically coupled to said barrier means sheet of flexible material.

4. The resuscitation mask of claim 1 wherein said means for a rescuers fingers to manually hold said sheet of flexible material are physical elements that may be grasped by fingers of the rescuer, said physical elements are positioned opposed to each other on either side of side of said one-way valve, said physical elements are secured to said sheet of flexible material and project away from the sheet of flexible material and towards the face of the victim when the mask is in use.

* * * * *